US012678533B2

(12) United States Patent
Zhang et al.

(10) Patent No.: US 12,678,533 B2

(45) Date of Patent: Jul. 14, 2026

(54) ***PAENIBACILLUS* STRAIN, AND HEMOSTATIC POLYSACCHARIDE PRODUCED BY SAME AND USE THEREOF**

(71) Applicant: Nanjing Southern Element Biotechnology Co., Ltd., Nanjing (CN)

(72) Inventors: Jianfa Zhang, Nanjing (CN); Changchang Kong, Nanjing (CN); Shijunyin Chen, Nanjing (CN); Bing Li, Nanjing (CN)

(73) Assignee: NANJING SOUTHERN ELEMENT BIOTECHNOLOGY CO., LTD., Nanjing City (CN)

( * ) Notice: Subject to any disclaimer, the term of this patent is extended or adjusted under 35 U.S.C. 154(b) by 497 days.

(21) Appl. No.: 18/196,609

(22) Filed: May 12, 2023

(65) Prior Publication Data

US 2024/0000993 A1 Jan. 4, 2024

(30) Foreign Application Priority Data

May 16, 2022 (CN) ......................... 202210528519.1

(51) Int. Cl.

| | |
|---|---|
| ***A61L 24/08*** | (2006.01) |
| ***A61K 31/716*** | (2006.01) |
| ***A61L 24/00*** | (2006.01) |
| ***A61P 7/04*** | (2006.01) |
| ***C12N 1/20*** | (2006.01) |
| ***C12P 19/04*** | (2006.01) |

(52) U.S. Cl.

CPC ............ *A61L 24/08* (2013.01); *A61K 31/716* (2013.01); *A61L 24/0015* (2013.01); *A61L 24/0036* (2013.01); *A61P 7/04* (2018.01); *C12N 1/20* (2013.01); *C12P 19/04* (2013.01); *A61L 2400/04* (2013.01)

(58) Field of Classification Search

CPC ....................................................... A61L 24/08

USPC ...................................................... 536/123.1

See application file for complete search history.

(56) References Cited

U.S. PATENT DOCUMENTS 10,738,275 B2 * 8/2020 Wu .......................... C12N 1/20

* cited by examiner

*Primary Examiner* — Traviss C Mcintosh, III

(74) *Attorney, Agent, or Firm* — Troutman Pepper Locke LLP

(57) ABSTRACT

The present disclosure provides a *Paenibacillus* strain, and a hemostatic polysaccharide produced by same and use thereof. In the present disclosure, a *Paenibacillus* sp. 1229 has a deposit number of CCTCC NO: M 2022553. A produced exopolysaccharide (EPS) Hemoadhican has a hemostatic function, and can be prepared as a hemostatic material in different dosage forms for different types of hemostasis. The hemostatic material has a high hemostatic speed, no need for applying pressures to the wound for a long time, safety and non-toxicity, desirable biocompatibility, and no requirement of removal after use. The material is suitable for the application of hemostasis in irregular bleeding such as solid organs in vitro or in vivo and diffuse bleeding.

4 Claims, 20 Drawing Sheets

Specification includes a Sequence Listing.

Gauze control group

Hemoadhican group

Vascular wounds were plugged

Without treatment

Hemoadhican powder

Control Hemoadhican

SEQUENCE LISTING

```
Sequence total quantity: 1
SEQ ID NO: 1            moltype = DNA  length = 1060
FEATURE                 Location/Qualifiers
source                  1..1060
                        mol_type = genomic DNA
                        note = 16S rDNA of the selected single colony strain
                        organism = Paenibacillus sp.
SEQUENCE: 1
acaatcttcg acggctggct ccttgcggtt accccaccgg cttcgggtgt tgtaaactct  60
cgtggtgtga cgggcggtgt gtacaagacc cgggaacgta ttcaccgcgg catgctgatc  120
cgcgattact agcaattccg acttcatgca ggcgagttgc agcctgcaat ccgaactgag  180
accgcctttt taggattcgc tccagatcgc tccttcgctt cccgttgtaa cggccattgt  240
```

-continued

```
agtacgtgtg tagcccaggt cataaggggc atgatgattt gacgtcatcc ccgccttcct  300
ccggtttgtc accggcagtc attctagagt gcccacctta aagtgctggc aactaaaatc  360
aagggttgcg ctcgttgcgg gacttaaccc aacatctcac gacacgagct gacgacaacc  420
atgcaccacc tgtctcctct gtccccgaag ggccgcccct atctctaggg gattcaaagg  480
gatgtcaaga cctggtaagg ttcttcgcgt tgcttcaaat taaaccacat actccactgc  540
ttgtgcgggt ccccgtcaat tcctttgagt ttcactcttg cgagcgtact ccccaggcgg  600
aatgcttaag gtgttaactt cggcaccaag ggtatcgaaa cccctaacac ctagcattca  660
tcgtttacgg cgtgaactac cagggtatct aatcctgttt gctccccacg ctttcgcgcc  720
tcagcgtcag ttacagccca gaaagtcgcc ttcgccactg gtgttcctcc acatctctac  780
gcatttcacc gctacacgtg gaattccact ttcctcttct gcactcaagt cttgcagttt  840
cagatgcgaa tcggggttga gccccgagat taaacacctg acttacaaaa ccgcctgcgc  900
gcgctttacg cccaaataat tccggacaac gcttgccccc tacgtattac cgcggctgct  960
ggnacgtagt tagccggggc tttctttctc aggtacgtca tagcagagca gtactctccc 1020
actcgttctt ccctnnaana gnagctttac gatccggaaa                      1060
```

*PAENIBACILLUS* STRAIN, AND HEMOSTATIC POLYSACCHARIDE PRODUCED BY SAME AND USE THEREOF

CROSS REFERENCE TO RELATED APPLICATION

This patent application claims the benefit and priority of Chinese Patent Application No. 202210528519.1, filed with the China National Intellectual Property Administration on May 16, 2022, the disclosure of which is incorporated by reference herein in its entirety as part of the present application.

REFERENCE TO SEQUENCE LISTING

A computer readable XML file entitled "GWP20230301417_148797_000320", that was created on Sep. 18, 2023, with a file size of about 3,042 bytes, contains the sequence listing for this application, has been filed with this application, and is hereby incorporated by reference in its entirety.

TECHNICAL FIELD

The present disclosure belongs to the technical field of microbial exopolysaceharides (EPSs), and relates to a *Paenibacillus* strain, and a hemostatic polysaccharide produced by same and use thereof.

BACKGROUND

In the first aid of sudden accidents, surgery and in war, 50% of the deaths are caused by massive bleeding. Studies have shown that the quick hemostasis rescue of the injured within 10 min of injury is a key factor in determining their survival. Hemostatic materials are an important means to stabilize injuries and reduce mortality during pre-hospital first aid, and the hemostatic speed and hemostatic effect of the hemostatic materials are directly related to life safety of the wounded. An ideal hemostatic material should have the following characteristics: I, a powerful hemostatic function that is capable of controlling massive bleeding from veins and arteries within 2 min; II, no need for additional mixing process and other equipment before use; III, convenience in use, with only simple operation steps for completing hemostasis; IV, light weight, durability, portability, and availability in harsh environments; V, stability in a wide temperature range (with an ideal temperature of −10° C. to 55° C.), and a long shelf life (at least 2 years of validity); VI, no damages to the human body and no risk of infection such as viruses; and VII, low cost. In addition, the ideal hemostatic material needs to have a strong ability to absorb wound exudate, less replacement times, antibacterial and anti-infection properties, long-term storage without irritation to the wound, sustained-release of drugs, and absorbability in vivo.

The hemostatic materials currently on the market and under research are divided into an injection type and an external use type according to their way of use. The injection type includes plasma, specific coagulation factors, platelets and other blood products, as well as compounds acting on coagulation cascade, and has a hemostatic mechanism to strengthen and supplement a coagulation cascade pathway of the human body. However, based on the above principle, this type of hemostatic materials inevitably has the disadvantage of inducing an immune response. In addition, the hemostatic materials also have defects such as difficulty in preservation and antigenic reactions. The external hemostatic materials have various forms, including tourniquet, colloid, powder and the like. The tourniquet and hemostat clamp can be used for hemostasis of large arteries, but are not suitable for hemostasis of special parts. Excessively tight a ligature on these special parts may cause tissue necrosis. As for a hemostatic gel, it is difficult to apply the hemostatic gel on a surface of the wound under the washing of a large blood flow, thereby severely limiting its application. Powdered hemostatic materials can be attached to the wound surface. In comparison, this type of materials can handle greater blood flow and can completely cover the wound. This form of product can effectively prevent death caused by massive hemorrhage, and buy valuable rescue time for the next step of hospitalization and treatment. However, microspherical hemostatic granules may break under pressure and enter the blood during use. During the treatment of a quick-acting hemostatic powder, attention should be taken to prevent a product from penetrating into blood vessels to form a thrombus when the product contacts the wound. Meanwhile, thorough debridement and suturing are required after the hemostasis.

Today, commonly used topical hemostatic materials on the market include: plain cotton gauze, zeolite-based hemostatic gauze, gelatin sponge, reconstituted oxidized cellulose sponge, and modified chitosan-based hemostatic powders. The most basic cotton gauze and bandages can only stop bleeding temporarily, and are gradually being replaced by new types of hemostatic materials. At present, the zeolite-based hemostatic gauze has the most in-depth researches, such as QuikClot produced by Z-Medica in the United States, and a quick-acting hemostatic powder developed in China with an A-type calcium zeolite molecular sieve as an active ingredient. However, the biggest disadvantage of the zeolite-based hemostatic material is that the heat released during hemostasis is likely to burn the wound and cause inflammation. Moreover, zeolites do not degrade in vivo. The biomacromolecular polymer hemostatic materials avoid the side effects of burns. However, the gelatin sponge can only locally absorb a small amount of blood, and the reconstituted oxidized cellulose sponge is expensive and can only control a small amount of bleeding. Chitosan hemostatic materials represented by Celox can effectively control large flow bleeding. However, these hemostatic materials are difficult to degrade, and the materials remaining in the wound must be removed before the surgery. Moreover, Celox hemostatic powders can cause deformation of red blood cells, such that a hemolysis rate of these materials cannot meet current requirements. In addition, all the above-mentioned external hemostatic materials rely on the enrichment of coagulation factors in human blood. Therefore, this type of hemostatic materials is not suitable for people with coagulation disorders and patients who are using anticoagulant drugs. Although some researches attempt to load thrombin and other components on the basis of raw materials, this kind of thinking also faces the aforementioned problems of injectable hemostatic agents.

In summary, there are various forms of hemostatic materials with different main components, and the hemostatic materials have a desirable clinical effect. However, these materials show disadvantages in quickly blocking bleeding vessels and stopping massive bleeding, have harsh conditions of use, and are difficult to degrade. In the surgical operation of patients who have used anticoagulant drugs and lost coagulation function, it is more difficult for ordinary hemostatic materials to meet the anticoagulant and hemostatic requirements during the operation. Accordingly, it has become a top priority to develop a new hemostatic material with high efficiency, biosafety, low cost, easy preparation, biodegradability, desirable biocompatibility, and independent of the blood composition of the wounded.

SUMMARY

A first objective of the present disclosure is to provide a *Paenibacillus* sp. 1229 for producing a medical biodegradable hemostatic polysaccharide Hemoadhican, where the strain has a deposit number of CCTCC NO: M 2022553, and was preserved in the China Center For Type Culture Collection located in Wuhan University, Wuhan, China on May 2, 2022.

A second objective of the present disclosure is to provide an exopolysaccharide (EPS) Hemoadhican produced by a *Paenibacillus* sp. 1229.

In the present disclosure, the EPS Hemoadhican has a structural formula as follows:

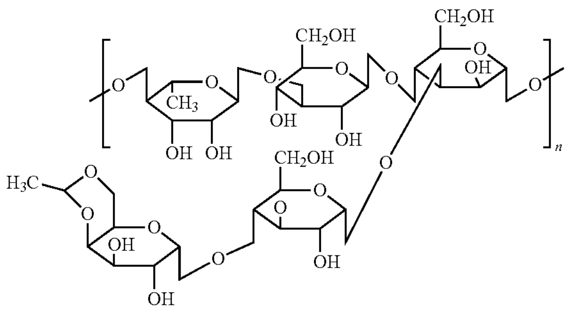

where n is 100 to 100,000; the EPS Hemoadhican includes glucose, mannose, galactose, and rhamnose in a molar ratio of 2:1:1:1, and has a glycosidic bond linkage as follows: →)-α-L-Rhap-(1→3)-β-D-Glcp-(1→4)[4,6-ethylene-α-D-Galp-(1→4)-α-D-Glc-(1→3)]-α-D-Manp-(1→.

A third objective of the present disclosure is to provide a production method of the EPS Hemoadhican, including the following steps:

step 1, fermentation: inoculating a seed solution of the *Paenibacillus* sp. 1229 into a fermentation medium, and conducting fermentation to obtain a fermentation broth; and step 2, purification: diluting the fermentation broth, conducting protein removal, adding 2 to 3 times a volume of ethanol to an obtained supernatant, conducting centrifugation to collect a resulting precipitate, and drying the precipitate to obtain a pure product of the EPS Hemoadhican.

In the present disclosure, the fermentation medium is a conventionally used medium for *Paenibacillus*. For example, a fermentation medium can be used, which has a pH value of 5 to 9, and includes the following components: 20 g/L to 50 g/L of a carbon source, 1 g/L to 4 g/L of a nitrogen source, 0.5 g/L to 2 g/L of $NaH_2PO_4$, 0.02 g/L to 0.1 g/L of $CaCl_2$), 0.1 g/L to 0.5 g/L of $MgSO_4$ $7H_2O$, 0.02 g/L to 0.06 g/L of $FeSO_4$ $7H_2O$, 0.005 g/L to 0.01 g/L of $MnSO_4$ $H_2O$, and 0.01 g/L to 0.02 g/L of $ZnCl_2$.

In the present disclosure, the carbon source in the fermentation medium is conventionally used by *Paenibacillus*, including one or more of glucose, sucrose, and starch.

In the present disclosure, the nitrogen source in the fermentation medium is conventionally used by *Paenibacillus*, including one or more of potassium nitrate, sodium nitrate, ammonium nitrate, peptone, and a yeast powder.

In the present disclosure, the *Paenibacillus* sp. 1229 is fermented at 26° C. to 32° C. for 48 h to 72 h.

In the present disclosure, a method of the protein removal adopts methods routinely used in the field, including but not limited to one or more methods selected from the group consisting of adding 0.05% to 0.2% of NaOH, filtration by a filter membrane of 20 nm to 2 μm, and ultrafiltration by an ultrafiltration membrane with a molecular weight cut-off of 5 kD to 50 kD.

In a specific example of the present disclosure, the purification specifically includes: mixing the fermentation broth with twice a volume of pure water, and adding NaOH to make a final concentration of the NaOH in an obtained mixture be 0.1; boiling the mixture for 20 min, and conducting filtration through a 1 μm filter to remove a precipitate I; adding 0.2% sodium acetate and 3 times a volume of the ethanol and stirring evenly, conducting centrifugation to collect a resulting precipitate II, and drying the precipitate II to obtain the pure product of the EPS Hemoadhican.

A fourth objective of the present disclosure is to provide use of the EPS Hemoadhican in preparation of a hemostatic material.

In the present disclosure, the hemostatic material uses EPS Hemoadhican as an active ingredient, and includes the EPS Hemoadhican alone, or includes the EPS Hemoadhican and a medically acceptable auxiliary material, or includes the EPS Hemoadhican and other drugs, or includes the EPS Hemoadhican, the medically acceptable auxiliary material, and the other drugs. The other drugs may be drugs with antibacterial and anti-inflammatory effects.

In the present disclosure, the hemostatic material has a dosage form selected from the group consisting of a powder, a sponge, and a gel.

In the present disclosure, the hemostatic material made of the EPS Hemoadhican is suitable for various bleeding conditions, including but not limited to visceral hemorrhage, arterial hemorrhage, or coagulopathy hemorrhage.

Compared with the prior art, the present disclosure has the following advantages:

(1) In the present disclosure, the EPS Hemoadhican has a unique chemical structure, is in the shape of a brush, and has strong attachment to vascular tissues.

(2) In the present disclosure, the EPS Hemoadhican has desirable biocompatibility and is easy to store and take under dry conditions. When being used as a hemostatic material, the Hemoadhican can absorb part of the blood to form a hemostatic plug by contacting the bleeding wound, forming a strong attachment force to the blood vessel tissues, thereby blocking the bleeding points and completely preventing the blood from exudation.

(3) In the present disclosure, the EPS Hemoadhican easily forms a hydration layer on its surface after absorbing water. When being used as a hemostatic material, the Hemoadhican can prevent moisture from penetrating inside to form phase separation, and can also prevent the hemostatic powder from penetrating into blood vessels to avoid vascular occlusion.

(4) In the present disclosure, when the EPS Hemoadhican is used as a hemostatic material, the EPS Hemoadhican not participated in hemostasis has low attachment and is easy to be peeled off from a hemostatic gel formed on the wound surface. In this way, a cleaning ability of the Hemoadhican on the wound surface is more obvious compared to that of highly-adherent materials.

(5) In the present disclosure, when being used as a hemostatic material, the EPS Hemoadhican does not rely on blood components such as platelets, calcium ions, and blood cells for hemostasis. The Hemoadhican can form a viscous gel-like hemostatic plug when meeting water, and also has an excellent hemostatic effect on abnormal coagulation models.

BRIEF DESCRIPTION OF THE DRAWINGS

FIG. 4A is a full spectrum, and FIG. 4B is an anomeric carbon zone;

FIG. 7A is the photo of each group at 15 min and 90 min, and FIG. 713 is the hemolysis rate of each group at 90 min;

DETAILED DESCRIPTION OF THE EMBODIMENTS

Figure 1:
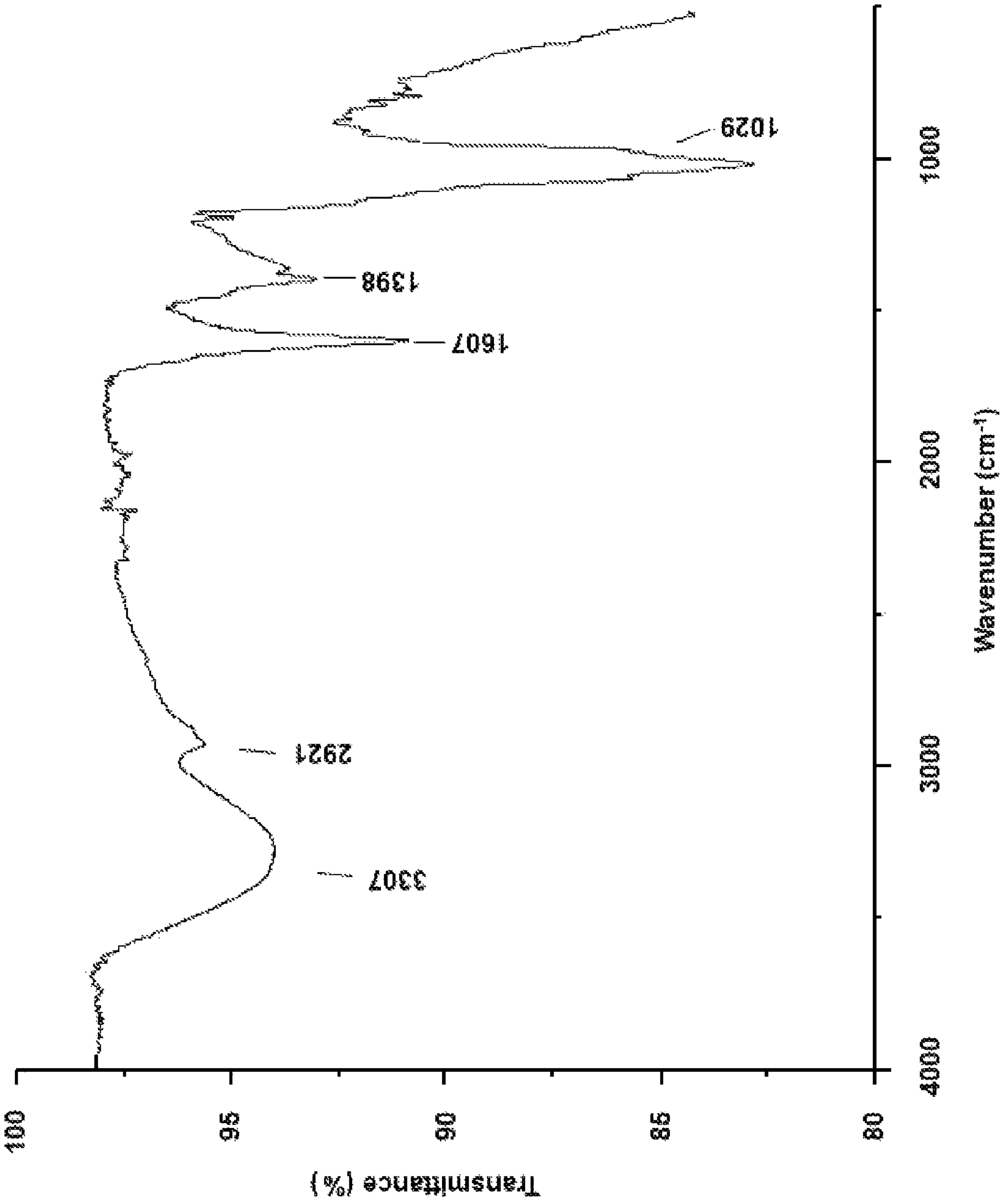
FIG. 1 shows an infrared absorption spectrum of the EPS Hemoadhican produced by a *Paenibacillus* sp. 1229.

Unless otherwise specified, all technical and scientific terms used in the present disclosure have the same meaning as commonly understood by one of ordinary skill in the technical field to which the present disclosure belongs. The specific embodiments and examples described below are for the purpose of illustration only, rather than limiting the present disclosure. Unless otherwise specified, the reagents or materials used in the following examples can be purchased commercially or synthesized by referring to existing methods. The present disclosure is described in more detail below with reference to the examples and accompanying drawings.

Example 1 Screening of *Paenibacillus* sp. 1229, Identification of 16S Sequence, and Fermentation Purification of EPS 1. Screening of *Paenibacillus* sp. 1229:

(1) A screening medium had a pH value of 7.2, and included the following components: 1 g/L of $KH_2PO_4$, 0.1 g/L of $CaCl_2$, 0.3 g/L of $MgCl_2 \cdot 6H_2O$, 0.0125 g/L of $FeSO_4$, 2 g/L of $KNO_3$, and 20 g/L of sucrose. A solid medium additionally required 15 g/L of agar. The medium was sterilized at 121° C. for 20 min.

(2) Screening method: soil from Nanjing Garden was placed into a 2 mL EP tube, added with 1 mL of normal saline, shaken evenly, and centrifuged at 50 g for 1 min to remove precipitated soil particles. 500 μL of an obtained supernatant I was aspirated and centrifuged at 12,000 g for 3 min, and an obtained supernatant II was discarded. Obtained precipitated bacterial cells were pipetted with 1 mL of normal saline, washed, centrifuged, and dissolved in 200 μL of normal saline to prepare a soil leachate. The soil leachate was diluted and coated on a solid plate medium, and cultured at 28° C. for 2 d to 3 d. After colonies grew, a single colony with sticky polysaccharides on the surface was selected according to morphological characteristics of the colony, diluted and spread on a new solid medium, and cultured at 28° C. After new colonies grew, a new single colony was selected for dilution and spreading. The above processes were repeated until colonies grown on the solid medium were monomorphic. The colonies were tested for their fermentative potential with liquid screening media.

2. Molecular identification: the 16S rDNA of the selected single colony strain (SEQ ID NO: 1 in the sequence table) was compared by Blast. According to Blast comparison, the strain had a sequence similarity of 98.35% to *Paenibacillus phyllosphaerae* strain PALXIL04, a sequence similarity of 98.06% to *Paenibacillus xanthanilyticus* strain AS7, and a sequence similarity of 97.96% to *Paenibacillus aurantiacus* strain RC11. Therefore, the strain was identified as *Paenibacillus* and named *Paenibacillus* sp. 1229.

3. Production and purification methods of EPS Hemoadhican produced by a *Paenibacillus* sp. 1229:

(1) A liquid fermentation medium used had a pH value of 7 and included: 30 g/L of sucrose, 3 g/L of $KNO_3$, 1 g/L of $NaH_2PO_4$, 0.07 g/L of $CaCl_2$, 0.2 g/L of $MgSO_4 \cdot 7H_2O$, 0.0375 g/L of $FeSO_4 \cdot 7H_2O$, 0.003 g/L of $MnSO_4 \cdot H_2O$, and 0.0075 g/L of $ZnCl_2$. A solid medium further included 15 g/L. of an agar powder on the basis of the liquid medium components.

(2) Fermentation process: a single colony was selected on a solid plate and cultured for 2 d at 28° C. and 230 rpm to obtain high-viability colonies. The high-viability colonies were selected into 10 mL of a liquid medium, and cultured for 2 d at 28° C. and 230 rpm to obtain a seed solution. The expanded fermentation was conducted on the seed solution according to an inoculation ratio of 2%, and continued to cultivate for 2 d to 3 d to obtain a high-viscosity fermentation broth.

(3) Purification: NaOH and a filtration method were adopted for the purification, including: the fermentation broth was mixed with twice a volume of pure water, and the NaOH was added to make a final concentration of the NaOH in an obtained mixture be 0.1; the mixture was boiled for 20 min, and filtration was conducted through a 1 μm filter to remove a precipitate I; 0.2% sodium acetate and 3 times a volume of the ethanol were added and stirred evenly, centrifugation was conducted to collect a resulting precipitate II, and the precipitate II was dried to obtain a pure product of the EPS Hemoadhican.

Example 2 Structural Analysis of EPS Hemoadhican

For the pure product of the Hemoadhican polysaccharide, a structure was analyzed and deduced using techniques such as infrared spectroscopy, high-performance liquid chromatography (HPLC), gas chromatography-mass spectrometry (GC-MS), and nuclear magnetic resonance (NMR). The structure was analyzed as follows:

The pure product of the Hemoadhican polysaccharide was tested by an infrared scanning instrument NICOLETIS10 (Thermo Fisher Scientific) and its existing functional groups were analyzed. The specific test process included: a pressed potassium bromide blank sheet was put on a sample holder of a sample chamber of the infrared scanning instrument, and a reference background spectrum for collection was confirmed. A sample to be tested was put into the spectrometer and scanned. A dosage of the sample was 2 mg to 5 mg each time. The infrared test results were shown in FIG. 1, the pure product of the Hemoadhican polysaccharide had obvious absorption peaks at 3,307, 2,921, 1,607, 1,398 and 1,029 $cm^{-1}$. A broad absorption peak at 3,307 $cm^{-1}$ belonged to the hydroxyl groups in various environments in polysaccharide molecules; an absorption peak at 2,921 $cm^{-1}$ came from stretching and bending vibrations of C—H in a sugar ring; an absorption peak at 1,607 $cm^{-1}$ came from a hydrogen bond formed by crystal water and sugar, an absorption peak at 1,398 $cm^{-1}$ came from an O—C—O bond in the acetal group; an absorption peak at 1,029 $cm^{-1}$ came from a C—C bond in the pyranose ring.

Figure 2:
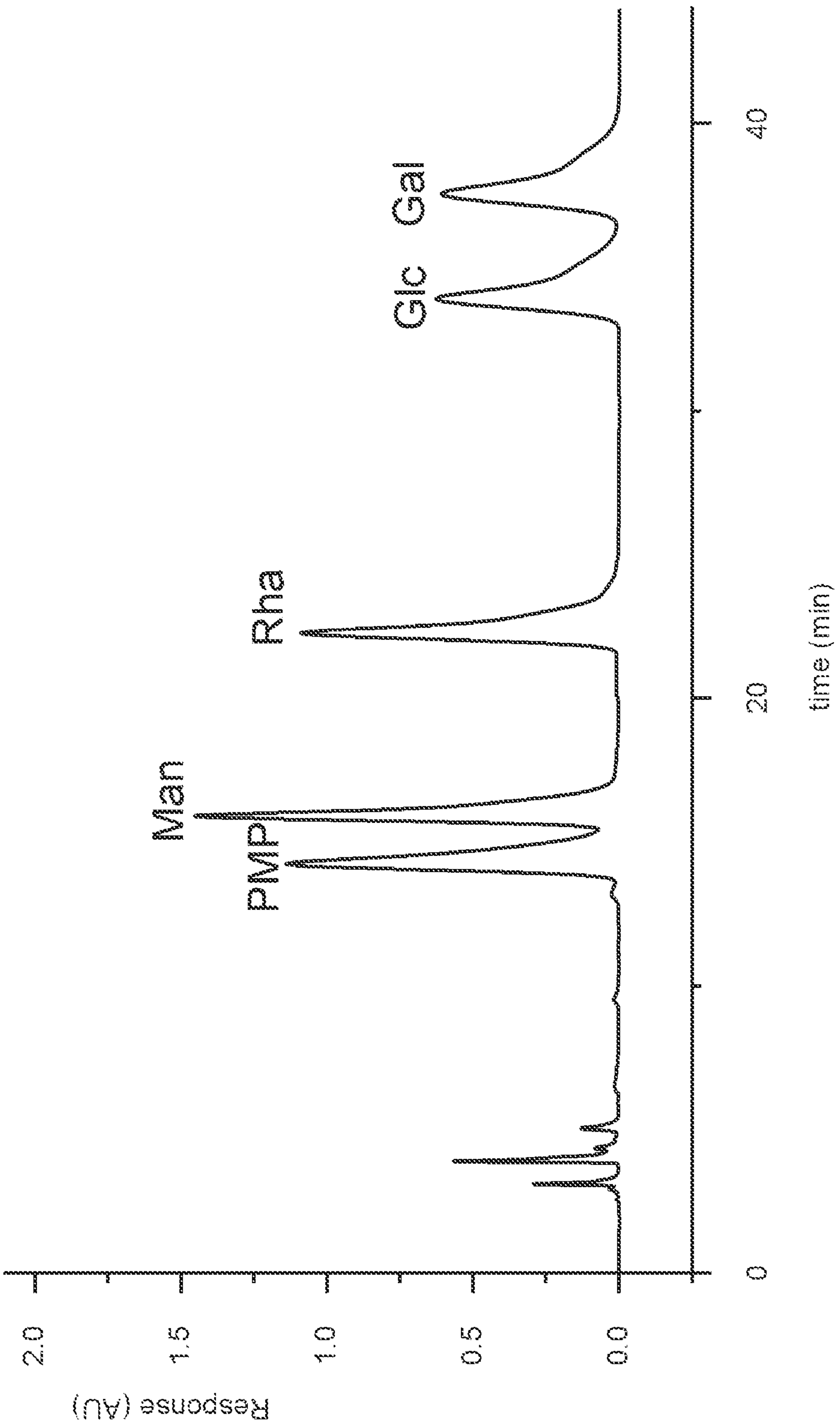
FIG. 2 shows a liquid chromatogram of component determination after the derivatization of the Hemoadhican polysaccharide; where marks in the figure are as follows: PMP represents a derivatization reagent 1-phenyl-3-methyl-5-pyrazolone, Man represents mannose, Rha represents rhamnose, Glc represents glucose, and Gal represents galactose.

Various monosaccharides presenting in the pure Hemoadhican polysaccharide were quantitatively analyzed by HPLC. The analysis process included: the microbial polysaccharide Hemoadhican was subjected to complete acid hydrolysis with trifluoroacetic acid, PMP derivatization, chloroform extraction, and water-phase filtration. The HPLC analysis was conducted by a Waters HPLC system (Waters Inc., USA) loaded with a Zorbax SB-Aq column (4.6 mm×150 mm, Agilent Technologies, Inc., USA). FIG. 2 showed a liquid chromatogram for the determination of monosaccharide components. As shown in FIG. 2, the Hemoadhican polysaccharide included glucose, mannose, galactose, and rhamnose in a molar ratio of 2:1:1:1.

Figure 3:
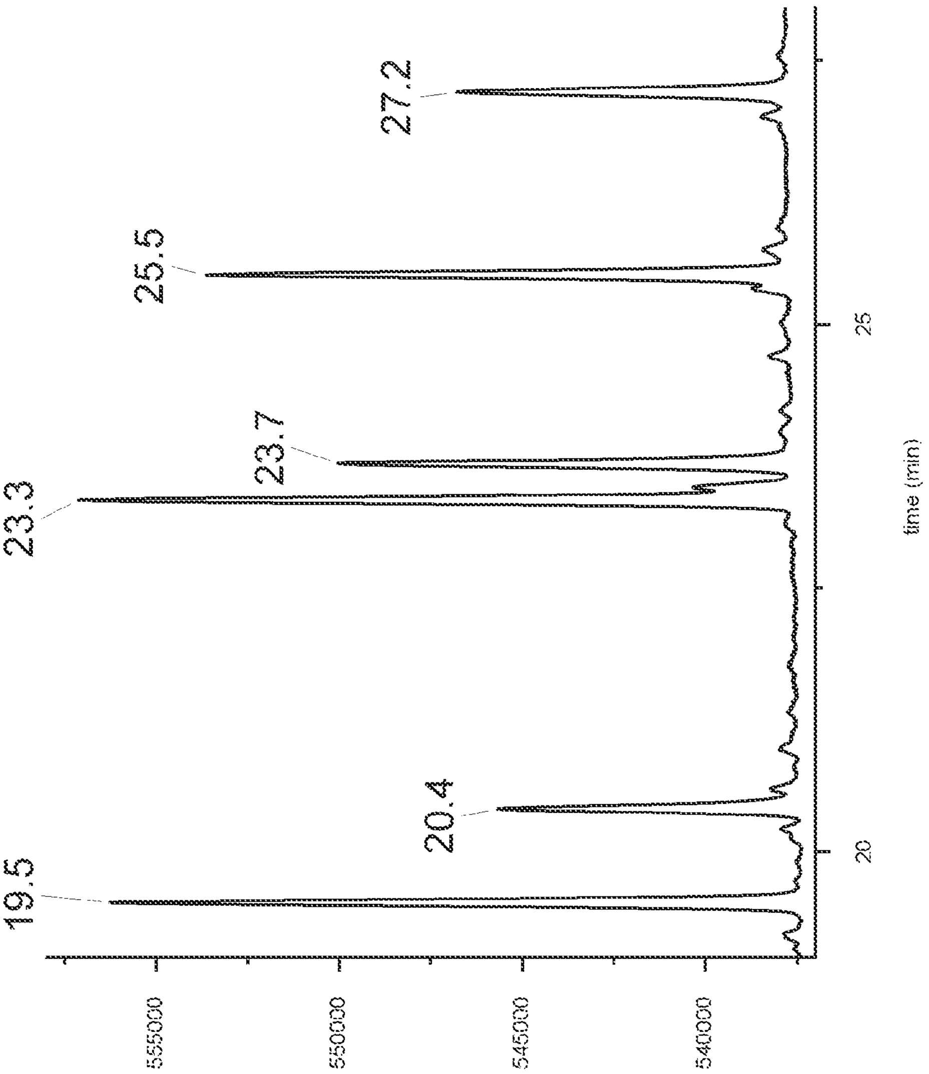
FIG. 3 shows a gas chromatogram of the Hemoadhican polysaccharide after methylation and acetylation treatments.

The glycosidic bond type of the Hemoadhican polysaccharide was analyzed by GC-MS. The analysis process included: exposed hydroxyl groups in the polysaccharide were marked by methylation, and the polysaccharide was hydrolyzed to break the glycosidic bond to expose the corresponding hydroxyl groups of the glycosidic bond. Acetylation was conducted to modify these hydroxyl groups. After the above steps, the polysaccharide was transformed into various monosaccharide derivatives that were volatile and heat-stable. The monosaccharide derivatives with different numbers of acetyl groups or different spatial positions were separated by gas chromatography (Thermo Scientific ISQ LT, USA) equipped with a TG-200MS column, so as to identify the types of glycosidic bonds of the polysaccharide. The results of the gas chromatography were shown in FIG. 3. Combined with mass spectrometry data, it was seen that the Hemoadhican polysaccharide included 1,3-linked-Rha with peak time of 19.5 min, 1,3-linked-Glc with peak time of 23.3 min, 1,4-linked-Glc with peak time of 23.7 min, 1,3,4-linked-Man with peak time of 25.5 min, and 1,4,6-linked-Gal with peak time of 27.2 min. The 1,4,6-linked-Gal was presumed to be located at the end of the branch chain, with modification groups attached to the 4th and 6th carbon atoms on it.

Figure 4A:
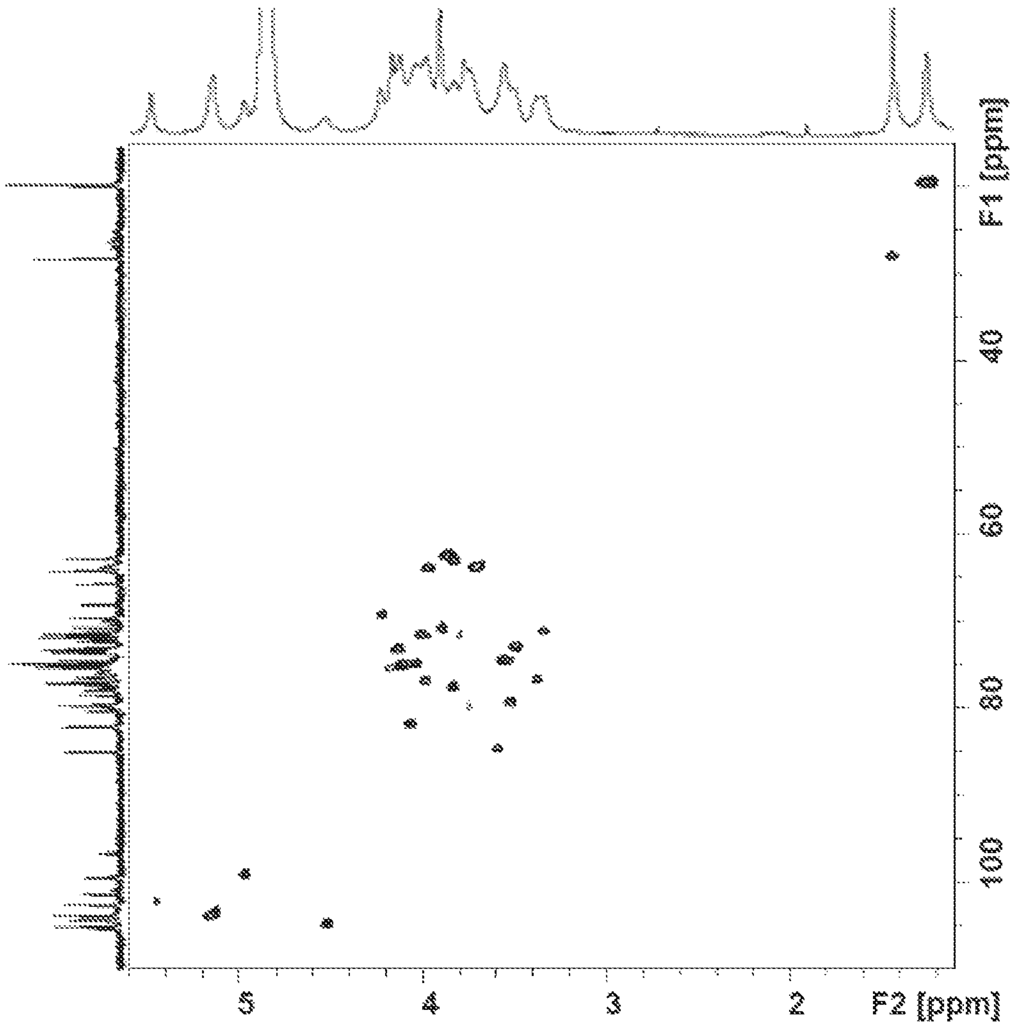
FIGS. 4A-B show heteronuclear single quantum coherent NMR spectrums of the Hemoadhican polysaccharide, where
Figure 4B:
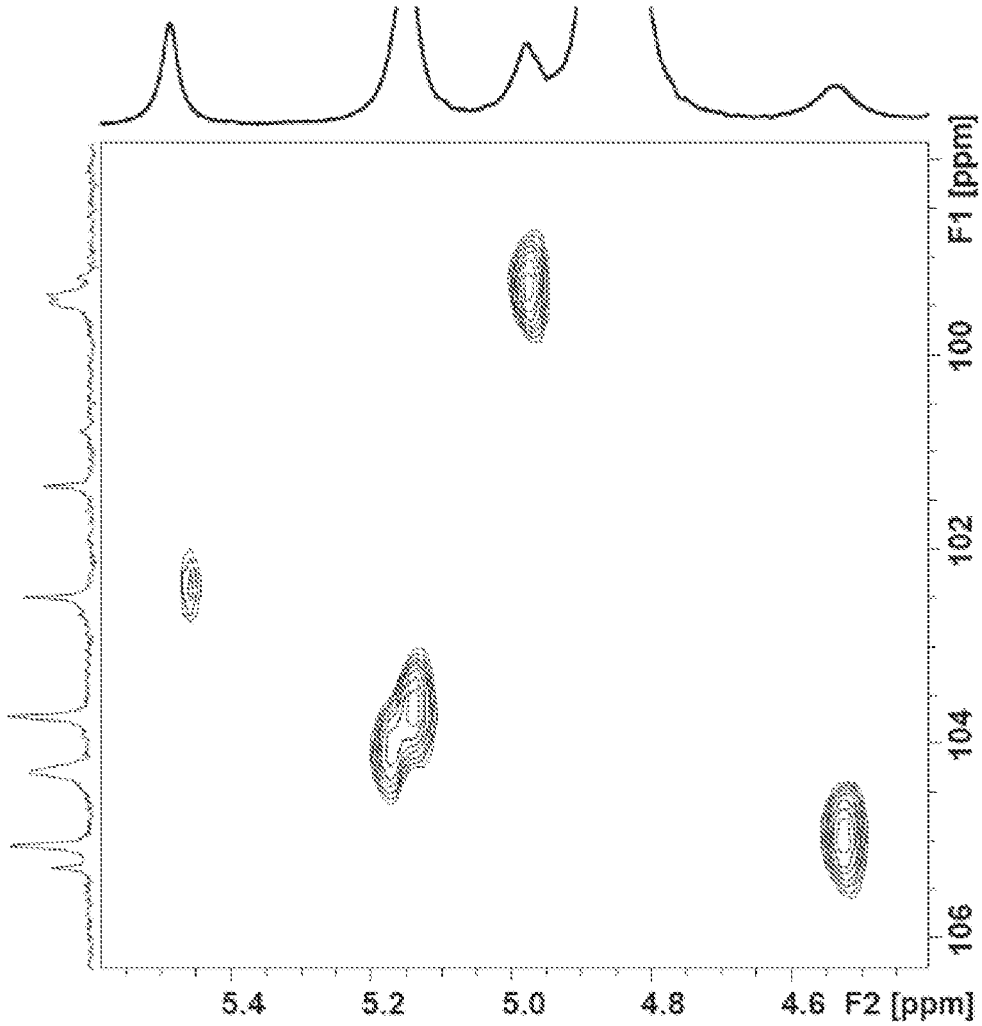

A linkage sequence of the Hemoadhican polysaccharide was analyzed by NMR. The analysis process included: the Hemoadhican polysaccharide was partially acid-hydrolyzed with trifluoroacetic acid, dissolved in $D_2O$ and deuterated, and TMSP was added as an internal standard. The NMR analysis was conducted with a Bruker Avance 500 MHz analyzer (Bruker, Karlsruhe, Germany), and an obtained heteronuclear single quantum coherent NMR spectrum was shown in FIGS. 4A-B.

Example 3 Molecular Weight Determination of Hemoadhican Polysaccharide

Figure 5:
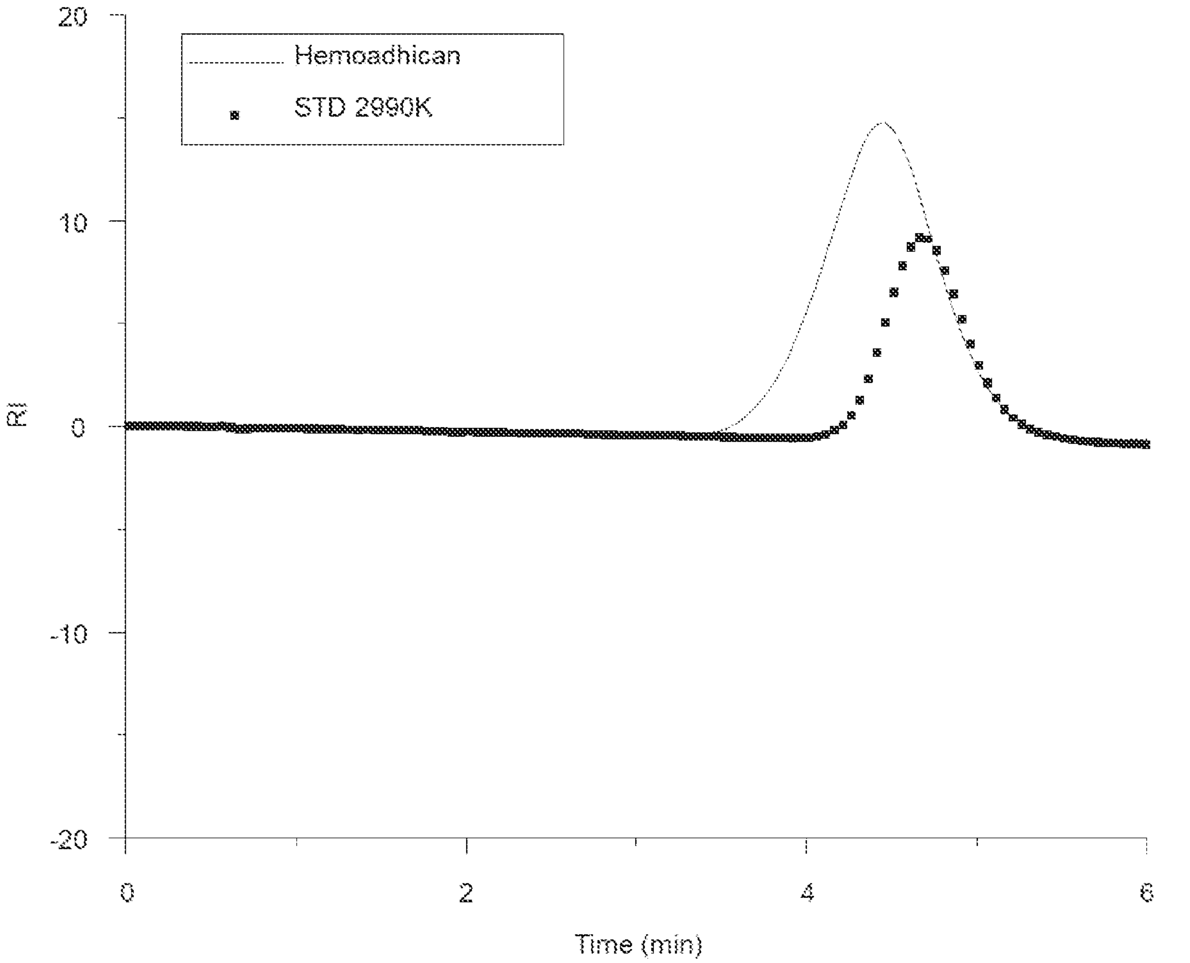
FIG. 5 shows a liquid chromatogram of molecular weight measurement of the Hemoadhican; where the figure, a solid line represents the Hemoadhican, and a dashed line represents a 2,990 kDa dextran standard.

The purified polysaccharide Hemoadhican was dissolved in deionized water, and its molecular weight was measured by gel permeation chromatography (TSK gel supermultipore PW-H column). A standard curve was calculated using 97 kDa to 2, 990 kDa of dextran. The results were shown in FIG. 5, and the final calculation showed that the Hemoadhican had a number average molecular weight of $1.21\times10^4$ kDa and a weight average molecular weight of $2.37\times10^4$ kDa.

Figure 6A:
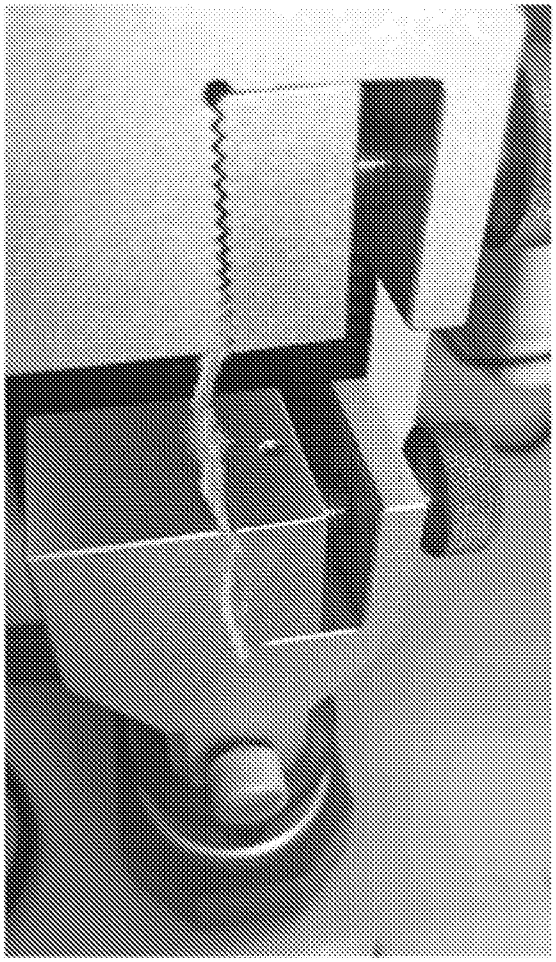
FIGS. 6A-B show experimental results of mouse skin attachment tension in vitro.
Figure 6B:
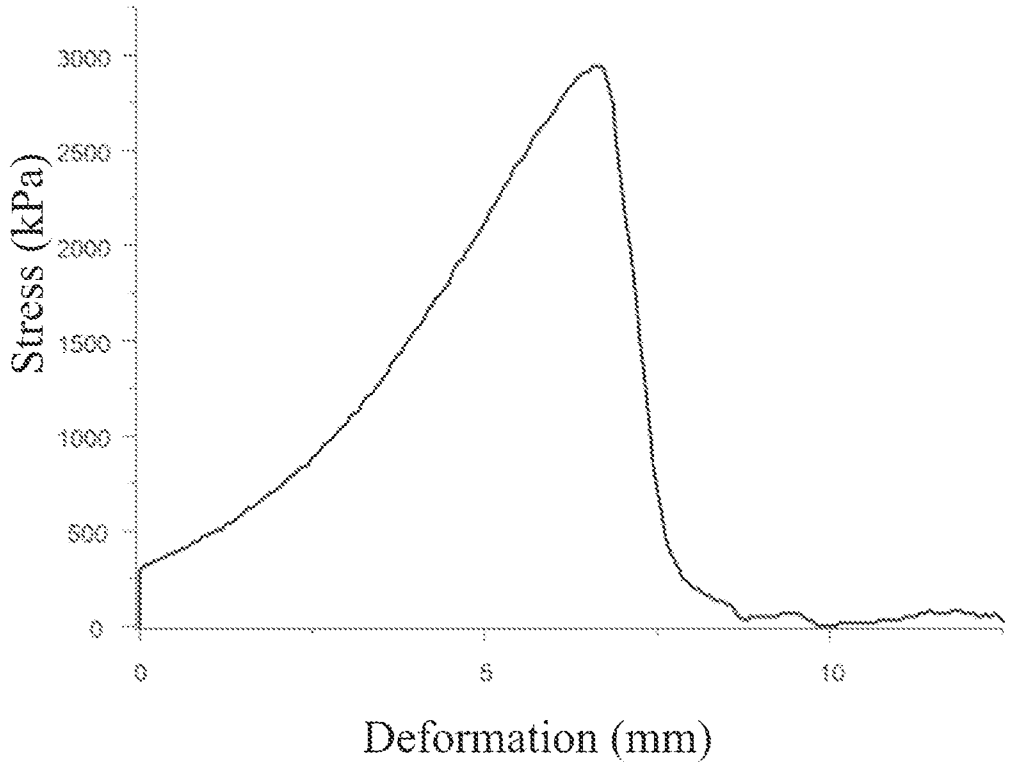

Example 4 Determination for Attachment of In Vitro-Simulated Polysaccharide Hemoadhican in Wound Environment The viscosity performance of the material in the wound environment was simulated in vitro: a polysaccharide Hemoadhican powder was placed between two overlapping parts of 30 mm×10 mm mouse skin, and a small amount of water was added to wet the powder into a colloid, and the variation of a single lap tensile shear strength of the colloid with a stretching deformation length was determined by a tensile test. The experimental process was shown in FIG. 6A, and the results were shown in FIG. 6B. After the two pieces of mouse skin were stretched and deformed by 6.57 mm, a tensile shear stress reached 2,944 kPa. At this moment, the Hemoadhican colloid used for sticking in the middle broke, indicating that the polysaccharide Hemoadhican could effectively withstand the impact without detaching from the wound.

Example 5 Hemoadhican Polysaccharide Hemolysis Rate and Biocompatibility Test

As a substance that directly interacts with blood, hemostatic materials must meet certain standards in terms of hemolysis rate and biocompatibility to achieve a desirable application prospect.

Figure 7A:
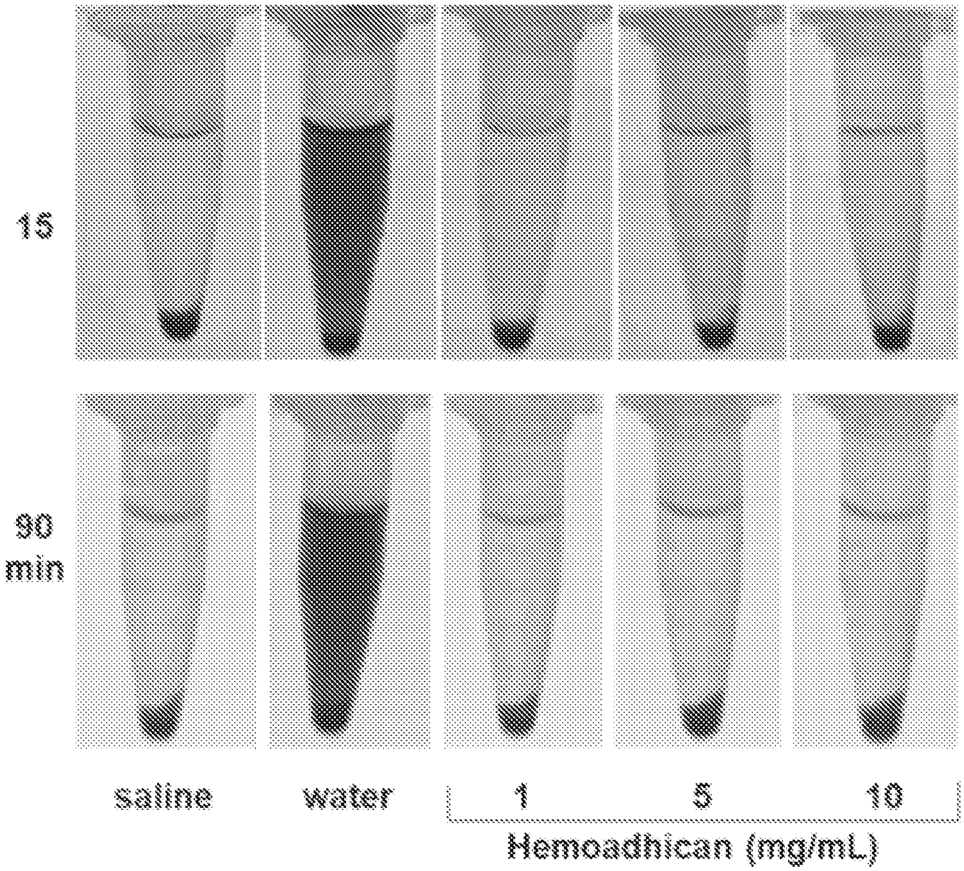
FIGS. 7A-B show test results of a hemolysis rate, where
Figure 7B:
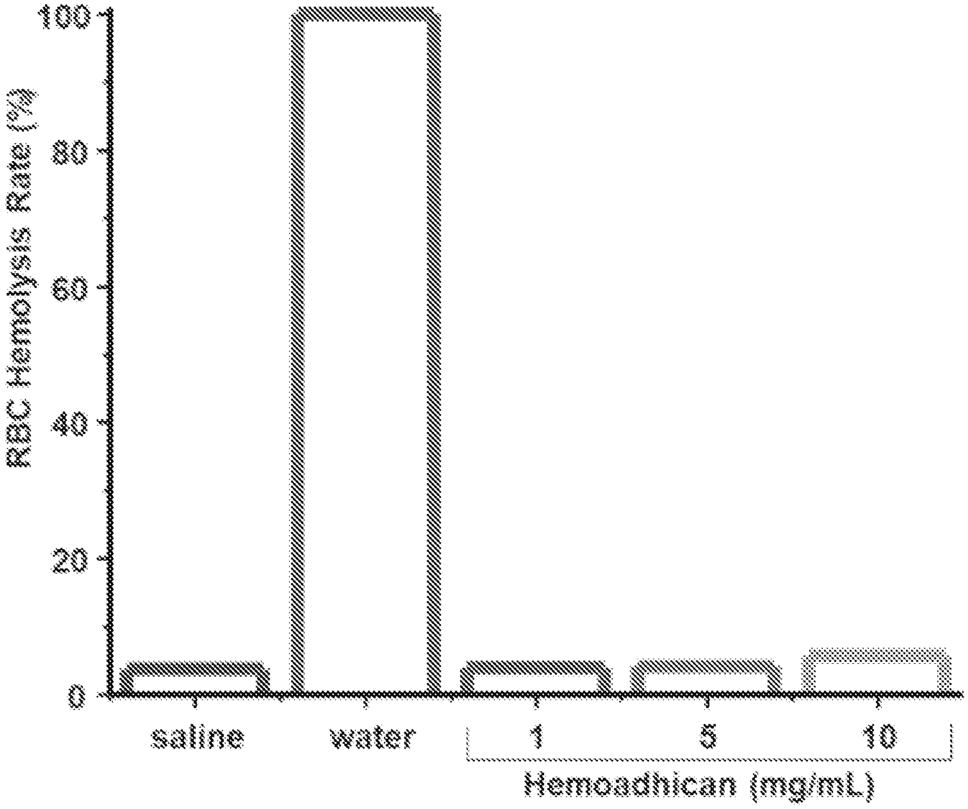

The collected whole blood anticoagulated with sodium citrate was diluted to 5 times with normal saline in a tube, and the Hemoadhican polysaccharide powder was added into the tube. An obtained sample was treated in a water bath at 37° C., photographs were taken at 15 min and 90 min, and the sample was centrifuged at 100 g for 5 min to remove red blood cells. 200 μL of a resulting supernatant was collected and measured to obtain an absorbance at 540 nm. During the test, normal saline was used as a positive control group, and deionized water was used as a blank control group, and the hemolysis rate was calculated. The results were shown in FIGS. 7A-B. The Hemoadhican polysaccharides at different concentrations each had a hemolysis rate of below 5%, which was close to that of normal saline, showing desirable biocompatibility.

Example 6 Hemoadhican Polysaccharide In Vitro and In Vivo Hemostatic Effect

1. In Vitro Blood Coagulation Index (BCI) and Red Blood Cell Adsorption Test (1) Establishment of In Vitro Coagulation Model:

Experimental animals were female Kunming mice, weighing 30 g to 35 g. The mice were housed under standard experimental conditions with a 12-hour light-12-hour dark cycle with free access to water and food. The eyeballs of the mice were protruded and hyperemic, and were quickly taken out with curved ophthalmic forceps. The mouse was turned upside down with the head down, and blood flowed out of the eye socket quickly. The blood was dripped into a 0.109 mol/L trisodium citrate aqueous solution for anticoagulant treatment, and mixed uniformly according to a volume ratio of 9:1 to obtain fresh anticoagulant blood. 300 g of whole blood anticoagulated with sodium citrate was centrifuged for 5 min, washed with normal saline, centrifuged 2 times, and finally added with the normal saline to obtain 5% packed red blood cells.

(2) Determination of BCI and Red Blood Cell Adsorption Rate:

(a) Determination of BCI: the experiment was divided into 3 groups according to different hemostatic materials, namely a blank control group, a Languan chitosan hemostatic powder (Qingdao Biotemed Biomaterial Co., Ltd.) group, and a Hemoadhican polysaccharide hemostatic powder group. 100 mg of the hemostatic material of each group was placed in a 90 mm glass petri dish, and 10 mM $CaCl_2$ was added to the whole blood anticoagulated with sodium citrate to relieve the anticoagulant function of sodium citrate. 200 μL of the whole blood was added dropwise onto the hemostatic material, and after 10 min, 5 ml of deionized water and a calcium chloride solution were added. Red blood cells that had not clotted into a clot underwent hemolysis, releasing hemoglobin (HGB). After treating on a horizontal shaker at 50 rpm/10 min, the absorbance of hemoglobin was detected at 540 nm by spectrophotometry. The BCI results were calculated as follows:

$$BCI(\%) = (\text{Abs}_{sample}/\text{Abs}_{blank}) \times 100\%,$$

where $\text{Abs}_{sample}$ was the absorbance of the experimental group at 540 nm; $\text{Abs}_{blank}$ was the absorbance of the blank group at 540 nm.

(b) Determination of red blood cell adsorption rate: the experiment was divided into 3 groups according to different hemostatic materials, namely a blank control group, a Languan chitosan hemostatic powder (Qingdao Biotemed Biomaterial Co., Ltd.) group, and a Hemoadhican polysaccharide hemostatic powder group. 10 mg of the hemostatic material of each group was placed in a screwed-mouth bottle, 200 μL of the 5% packed red blood cells were added and treated for 1 h, and washed with normal saline 3 times to remove unadsorbed red blood cells. The treated red blood cells were swollen with 5 mL of pure water, and the absorbance of hemoglobin at 540 nm was detected by spectrophotometry as above.

(3) Data Analysis

Figure 8A:
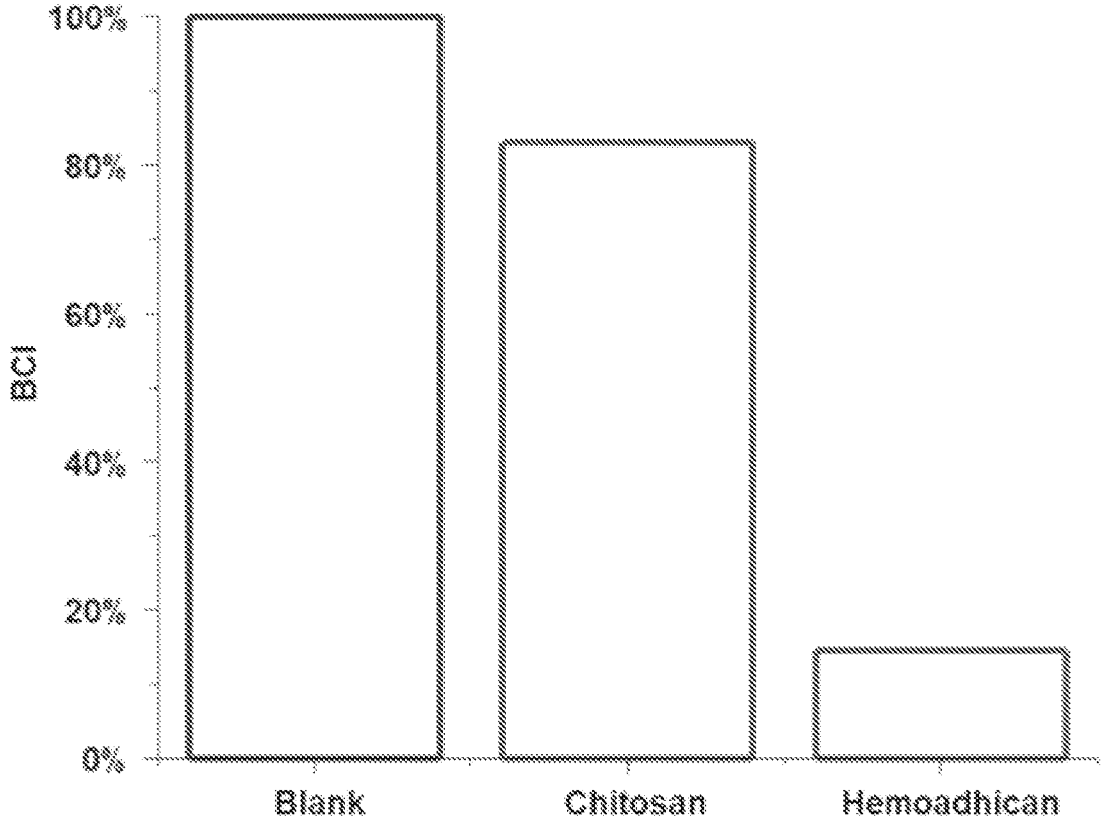
FIG. 8A shows BCI index results of an in vitro hemostasis test.
Figure 8B:
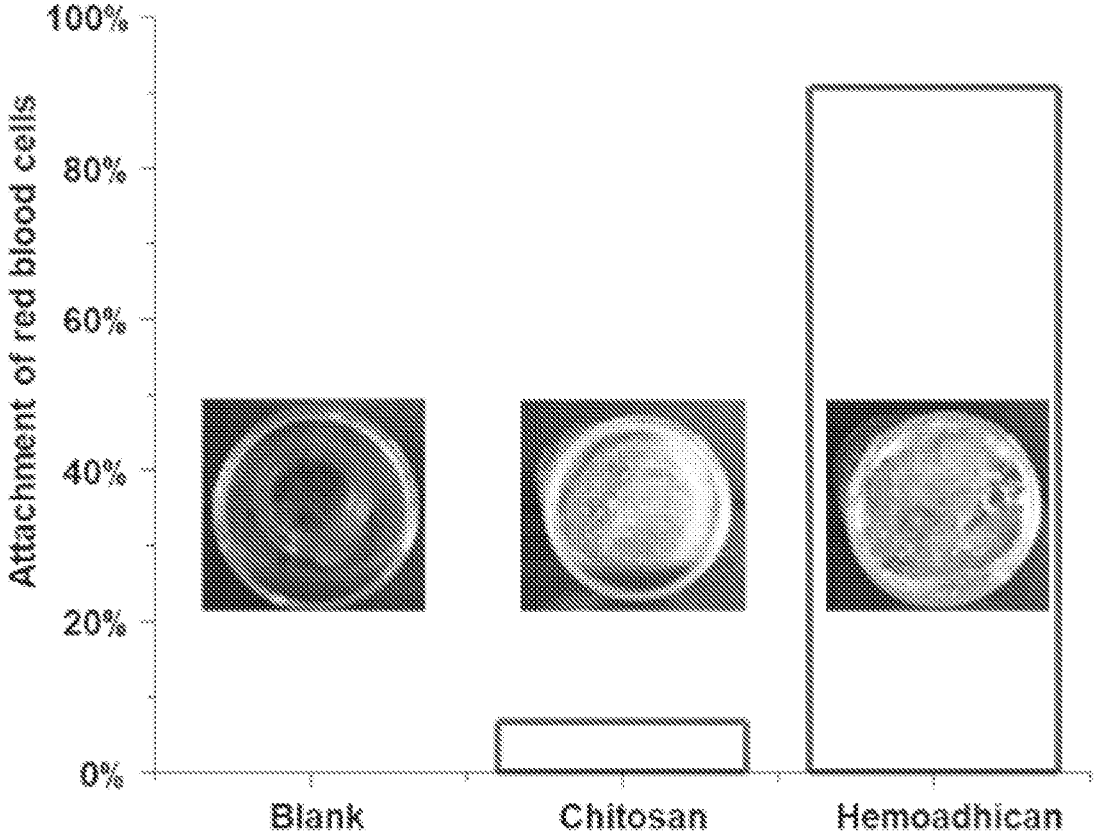
FIG. 8B shows red blood cell adsorption rate results.

A lower BCI index and a higher red blood cell adsorption rate indicated a better coagulation effect. As shown in FIGS. 8A-B, the Languan chitosan hemostatic powder group had a BCI of 83.1% and a red blood cell adsorption rate of 6.8%, while the Hemoadhican polysaccharide hemostatic powder group had a BCI of 14.5% and a red blood cell adsorption rate of 90.8%. This showed that the Hemoadhican polysaccharide hemostatic powder had significant coagulation ability in vitro.

2. Evaluation of Hemostatic Effect of Hemoadhican Hemostatic Sponge and Mouse Liver Hemostatic Experiment (1) Establishment of Animal Models:

Experimental animals were female Kunming mice, weighing 30 g to 35 g. The mice were housed under standard experimental conditions with a 12-hour light-12-hour dark cycle with free access to water and food. The mice were anesthetized by intraperitoneal injection of 5% chloral hydrate, and the experiment was started after confirming that the mice were completely anesthetized and had no eyelid reflex. The mice were randomly divided into two groups, where a first group was a blank control group (a blank test without giving any hemostatic material); a second group was a Hemoadhican hemostatic sponge group. A preparation method of the Hemoadhican hemostatic sponge included: Hemoadhican and water were prepared into a 2% hydrogel at a ratio of 2:98, and freeze-dried for 24 h to obtain the Hemoadhican hemostatic sponge.

(2) Determination of Hepatic Bleeding Volume:

The mice were fixed on an experimental table in a supine position, and their abdomen was opened layer by layer to expose the liver. A 1 cm wound was cut in the liver with a scalpel blade, and after 5 sec of free bleeding, the outflowing blood was wiped off. After the blood was wiped off on the wound surface of the control group, a filter paper was placed under the liver. The administration group was covered with the Hemoadhican hemostatic sponge immediately, and timing was started until the bleeding stopped. The hemostasis time and bleeding volume were recorded, and an average value was selected. The hemostasis time was a time from applying the hemostatic material to the cessation of bleeding; the bleeding volume was a difference in weight of the filter paper before and after hemostasis.

Figure 9:
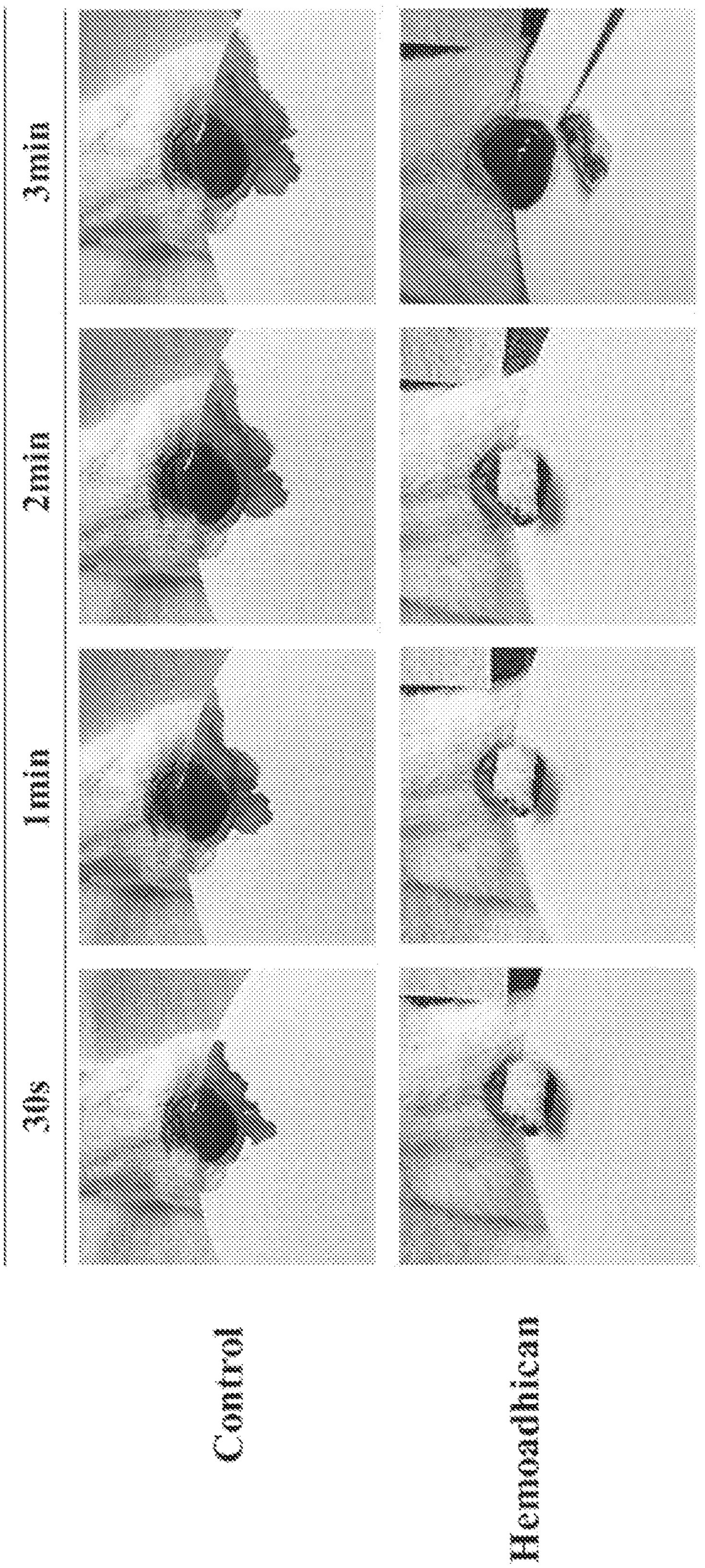
FIG. 9 shows experimental results of mouse liver hemostasis, where a side is a blank control group, and another side is a Hemoadhican polysaccharide sponge hemostasis group.

(3) Results and Analysis:

FIG. 9 showed results of the liver treatment, where the Hemoadhican hemostatic sponge group completely prevented the exudation of blood, and the filter paper had no weight difference.

3. Evaluation of Hemostatic Effect of Hemoadhican Polysaccharide Powder Hemostatic Material and Rat Carotid Artery Hemostatic Experiment (1) Establishment of Animal Models:

Experimental animals were female SD rats, weighing 220 g to 260 g. The mice were housed under standard experimental conditions with a 12-hour light-12-hour dark cycle with free access to water and food. The mice were anesthetized by intraperitoneal injection of 5% chloral hydrate, and the experiment was started after confirming that the mice were completely anesthetized and had no eyelid reflex. The experimental animals were randomly divided into two groups, a first group was a negative control group, and gauze was used to stop bleeding; a second group was a Hemoadhican polysaccharide powder hemostatic material group.

(2) Determination of Carotid Artery Bleeding Volume:

4 healthy adult SD rats were randomly divided into two groups. All animals were fasted (without water) for 12 h before operation. The rats were anesthetized by intraperitoneal injection of 3% pentobarbital sodium at 40 mg/kg of body weight. A longitudinal incision of about 2 cm was made on the midline of the neck, the muscle was cut open, and carotid artery was picked out. The carotid artery was cut open with a scalpel, after which the drug was administered and the wound was pressed with gauze. During the hemostasis, the gauze was pressed properly to ensure that the gauze was in contact with the wound. The weights of the gauze before and after the experiment were recorded, and the bleeding volume was calculated through a weight difference.

(3) Results and Analysis

Figure 10A:
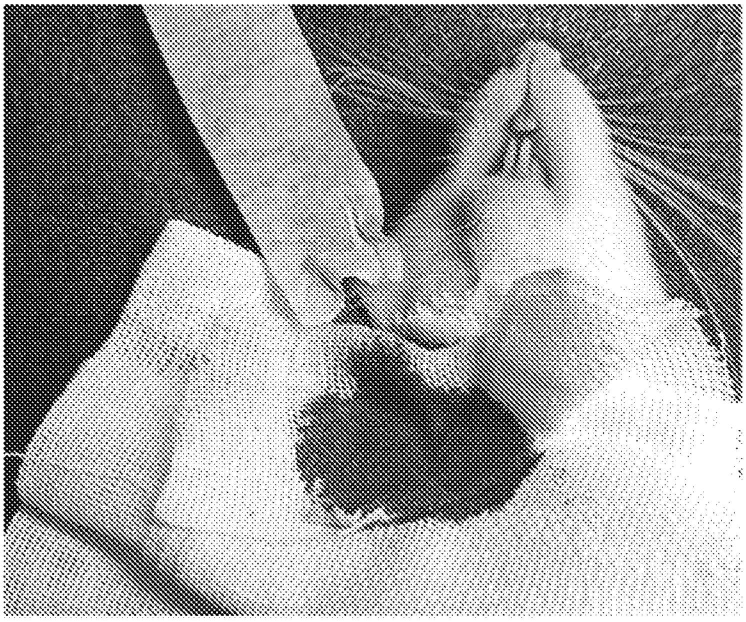
FIGS. 10A-C show experimental results of mouse carotid artery hemostasis.
Figure 10B:
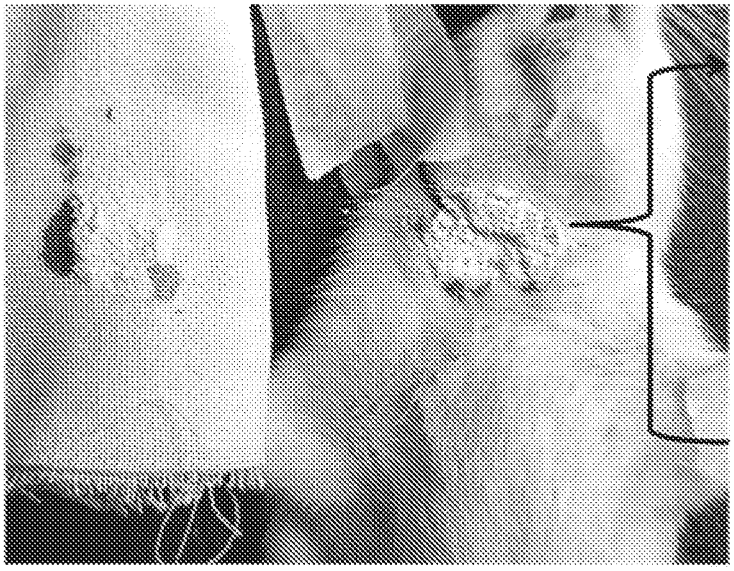
Figure 10C:

As shown in FIGS. 10A-C, the Hemoadhican polysaccharide powder significantly prevented blood outflow from the wound, reducing blood loss from 3.49 g in the control group to 0.02 g. Through further dissection, it was found that the Hemoadhican polysaccharide powder formed a get at the arterial wound to seal the wound. After peeling off the gel, it was found that the blood continued to flow normally. However, chitosan alone was not reported to be used in carotid artery hemostasis.

In summary, Hemoadhican polysaccharides exhibited excellent hemostatic properties in bleeding models of various organs. The main hemostatic mechanism was to seal the wound with a high-viscosity gel formed after dissolving the Hemoadhican polysaccharide to prevent blood loss.

Figure 11A:
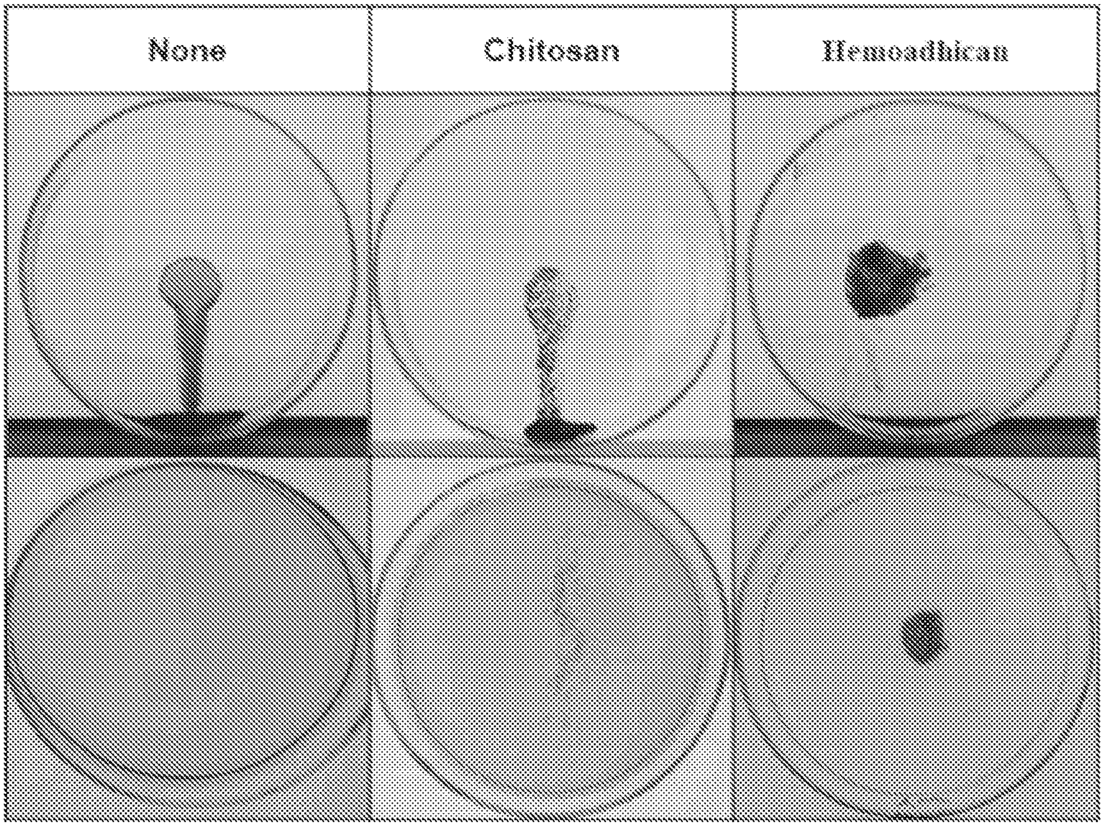
FIGS. 11A-B show BCI index of an in vitro anticoagulation model.
Figure 11B:
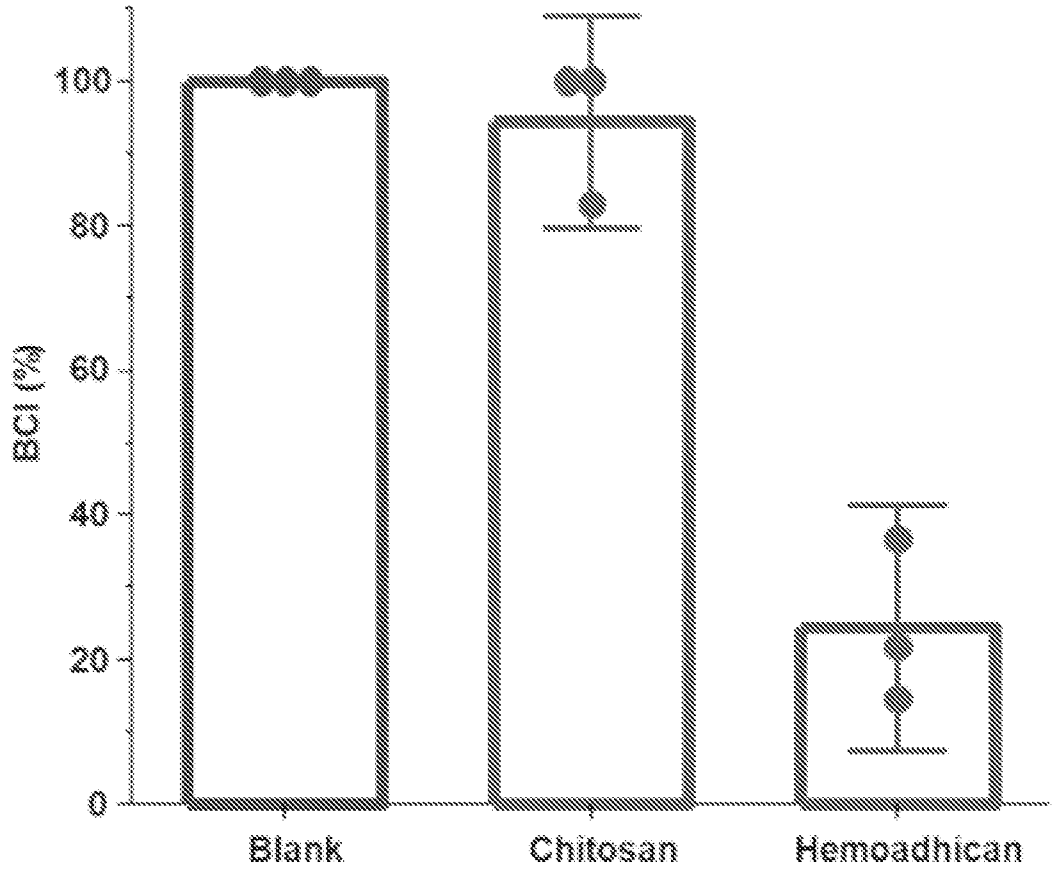

Example 7 Hemostatic Effect of Hemoadhican Hemostatic Material on Coagulation Disorder Model 1. In Vitro Coagulation Index of Hemoadhican Polysaccharide on Coagulation Disorder Model:

An experiment of the coagulation disorder model in vitro was the same as the in vitro BCI (%) experiment in Example 6, except that the calcium chloride solution was not added to cancel the inhibitory effect of sodium citrate. As shown in FIGS. 11A-B, in the whole blood experiment of coagulation disorder in vitro, the Languan chitosan hemostatic powder group had a BCI index of 94.2%, and the Hemoadhican polysaccharide hemostatic powder group had a BCI of 32.1%. This demonstrated that the Hemoadhican polysaccharide retained a comparable hemostatic capacity even in the coagulation disorder model. However, the chitosan hemostatic powder was almost ineffective for the coagulation disorder model.

2. Evaluation of Hemostatic Effect of Hemoadhican Powder Hemostatic Material and Tail-Docking Model of Heparinized Mice (1) Establishment of Animal Models:

Experimental animals were female Kunming mice, weighing 30 g to 35 g. The mice were housed under standard experimental conditions with a 12-hour light-12-hour dark cycle with free access to water and food. The mice were anesthetized by intraperitoneal injection of 5% chloral hydrate, and the tail vein injection of a heparin sodium solution was conducted for experiment after confirming that the mice were completely anesthetized and had no eyelid reflex. The mice were randomly divided into two groups, a first group was a control group, and gauze was used to stop bleeding; a second group was a Hemoadhican powder hemostatic material group.

(2) Determination of Tail Tip Bleeding Volume:

100 mg of the Hemoadhican powder hemostatic material was placed on gauze as a sample. The limbs of the mice were fixed on a mouse board, and a length of the tail was measured. The tail hung down freely, and ⅓ of the length of the tail was cut off with surgical scissors from the tail tip. After 5 sec of free bleeding, the tail was inserted into the sample or gauze. After 3 min of hemostasis, the tail was taken out for observation.

(3) Results and Analysis

Figure 12A:
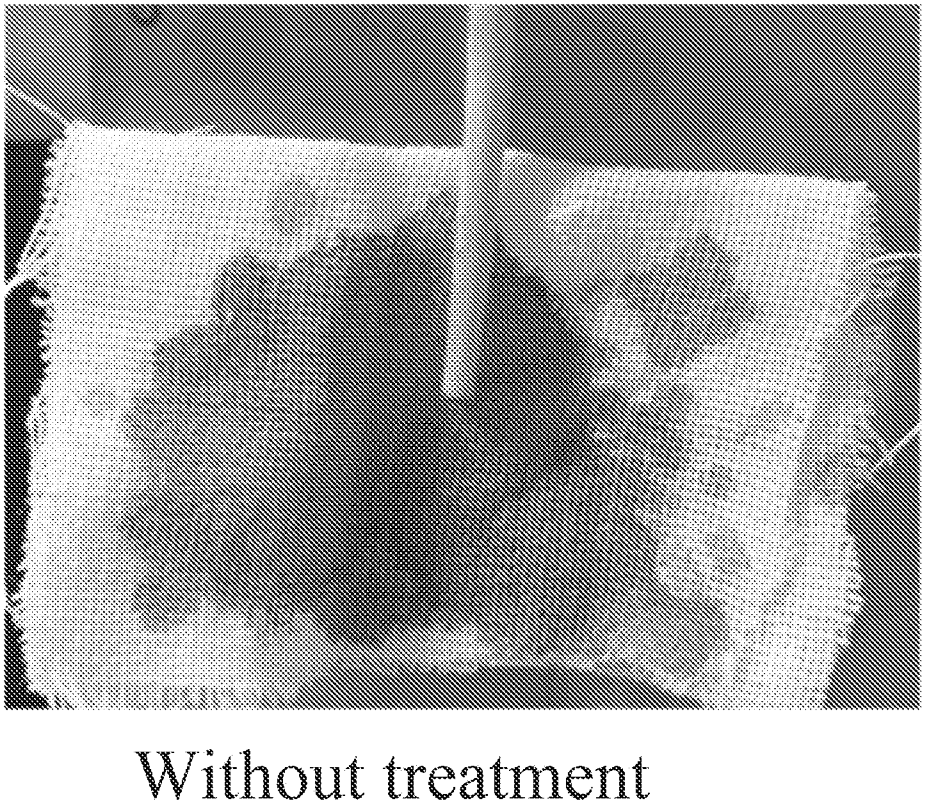
FIGS. 12A-B show experimental results of hemostasis in tail of mice injected with heparin.
Figure 12B:
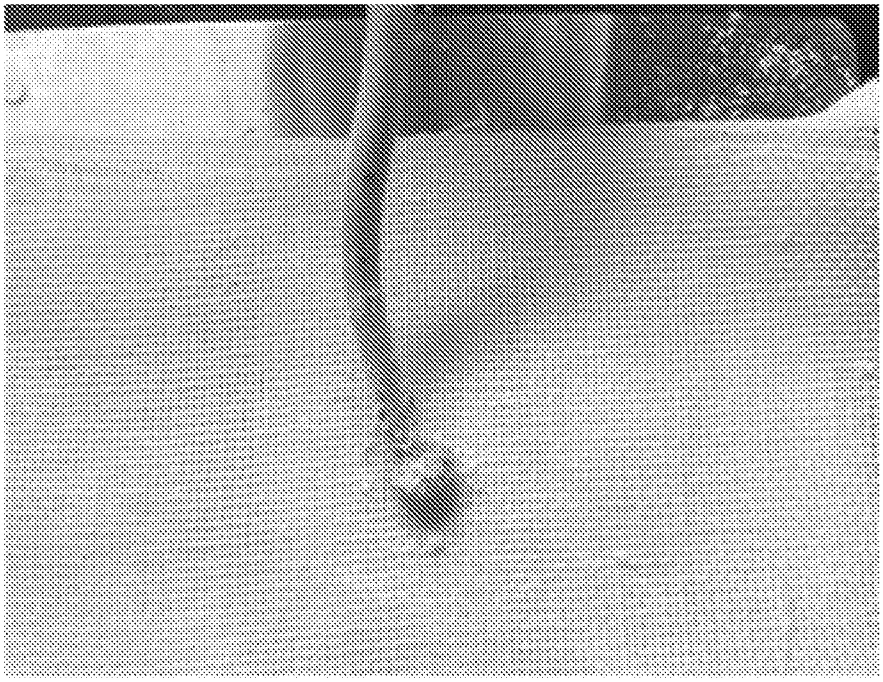

As shown in FIGS. 12A-B, the untreated control group bled 0.50 g within 3 min, while the Hemoadhican powder completely suppressed tail bleeding in heparin-treated mice.

Figure 13:
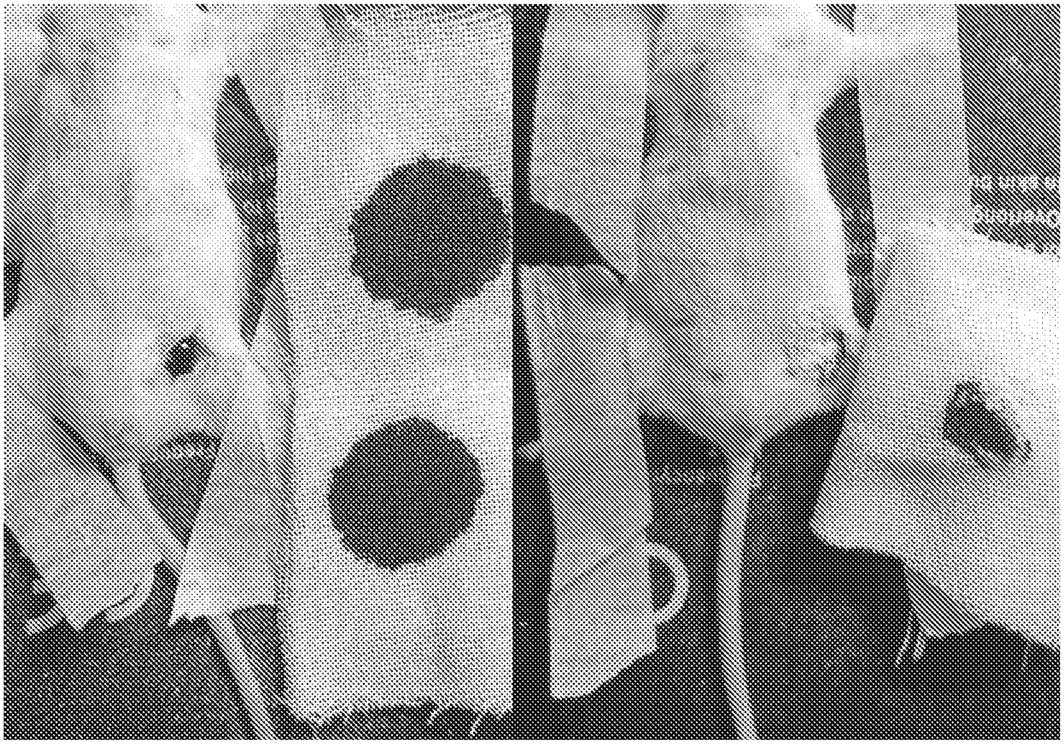
FIG. 13 shows experimental results of hemostasis in femoral artery of mice injected with heparin.

3. Evaluation of Hemostatic Effect of Hemoadhican Powder Hemostatic Material and Femoral Artery Hemostasis Experiment of Heparinized Mice (1) The femoral artery hemostasis experiment of the heparinized mice was the same as the rat carotid artery hemostatic experiment in Example 6, except that after the mice were anesthetized, the heparin sodium solution was injected into the tail vein, and then subsequent experimental operations were conducted. As shown in FIG. 13, the bleeding in the control group continued until execution, and had an average bleeding volume of 0.79 g within 3 min; while there was no visible bleeding in the experimental group, and an average bleeding volume was 0.12 g.

In summary, the Hemoadhican powder does not depend on blood components for hemostasis, and has an excellent hemostatic effect on coagulation disorder models.

The foregoing embodiments are merely intended to exemplarily explain the principles and effects of the present disclosure, rather than limit the present disclosure. Any person skilled in the art can make modifications or alterations to the foregoing embodiments without departing from the spirit and scope of the present disclosure. Hence, all equivalent modifications or changes made by those of ordinary skill in the art without departing from the spirit and technical teachings disclosed in the present disclosure should fall within the scope defined by appended claims to the present disclosure.

We claim:

1. A hemostatic material, comprising an exopolysaccharide (EPS) Hemoadhican produced by a *Paenibacillus* sp. 1229 with a deposit number of CCTCC NO: M 2022553, the EPS Hemoadhican has a structural formula as follows:

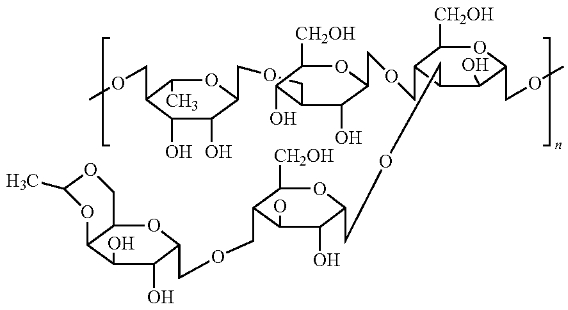

wherein n is 100 to 100,000; the EPS Hemoadhican comprises glucose, mannose, galactose, and rhamnose in a molar ratio of 2:1:1:1, and has a glycosidic bond linkage as follows:→)-α-L-Rhap-(1→3)-β-D-Glcp-(1→4) [4,6-ethylene-α-D-Galp-(1→4)-α-D-Glc-(1→3)]-α-D-Manp-(1→.

2. The hemostatic material according to claim 1, wherein the hemostatic material comprises the EPS Hemoadhican alone, or comprises the EPS Hemoadhican and a medically acceptable auxiliary material, or comprises the EPS Hemoadhican and other drugs, or comprises the EPS Hemoadhican, the medically acceptable auxiliary material, and the other drugs.

3. The hemostatic material according to claim 1, wherein the hemostatic material has a dosage form selected from the group consisting of a powder, a sponge, and a gel.

4. The hemostatic material according to claim 1, wherein the hemostatic material is used for treating visceral hemorrhage, arterial hemorrhage, or coagulopathy hemorrhage.

* * * * *